(12) United States Patent
Slany et al.

(10) Patent No.: US 7,105,689 B2
(45) Date of Patent: Sep. 12, 2006

(54) COMPOUND SUITABLE FOR USE AS A CATALYST OR FOR PRODUCING A CATALYST SYSTEM DERIVED FROM A BIS-PHOSPHORINANE

(75) Inventors: Michael Slany, Kirchheim (DE); Martin Schäfer, Grünstadt (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 315 days.

(21) Appl. No.: 10/467,232

(22) PCT Filed: Jan. 26, 2002

(86) PCT No.: PCT/EP02/00822

§ 371 (c)(1), (2), (4) Date: Aug. 6, 2003

(87) PCT Pub. No.: WO02/064249

PCT Pub. Date: Aug. 22, 2002

(65) Prior Publication Data

US 2004/0059157 A1    Mar. 25, 2004

(30) Foreign Application Priority Data

Feb. 9, 2001 (DE) ................. 101 06 348

(51) Int. Cl.
*C07F 17/02* (2006.01)

(52) U.S. Cl. ............... 556/18; 556/21; 568/13; 564/16

(58) Field of Classification Search ............... 564/16; 568/13; 556/18, 21
See application file for complete search history.

(56) References Cited

U.S. PATENT DOCUMENTS

| | | | |
|---|---|---|---|
| 4,257,973 A | | 3/1981 | Mrowca |
| 4,508,660 A | | 4/1985 | Sieja |
| 4,642,382 A | * | 2/1987 | Spivack et al. ............ 568/12 |
| 4,933,483 A | | 6/1990 | Burke et al. |
| 5,177,044 A | * | 1/1993 | van Doorn et al. ........ 502/162 |
| 5,177,230 A | * | 1/1993 | Burk ..................... 556/13 |
| 5,179,225 A | | 1/1993 | Drent et al. |
| 6,346,640 B1 | | 2/2002 | Slany et al. |

FOREIGN PATENT DOCUMENTS

| | | |
|---|---|---|
| DE | 25 41640 | 3/1977 |
| EP | 373 579 | 6/1990 |
| EP | 450 577 | 10/1991 |
| EP | 577 204 | 1/1994 |
| EP | 646 588 | 4/1995 |
| EP | 662 467 | 7/1995 |
| GB | 963418 | 7/1964 |
| GB | 1 497 046 | 1/1978 |
| WO | 96-19434 | 6/1996 |
| WO | 98-42717 | 10/1998 |
| WO | 00/42717 | 7/2000 |
| WO | 00/56695 | 9/2000 |
| WO | 02-00669 | 1/2002 |

* cited by examiner

Primary Examiner—Johann Richter
Assistant Examiner—Chukwuma Nwaonicha
(74) Attorney, Agent, or Firm—Novak Druce & Quigg, LLP; Jason D. Voight

(57) ABSTRACT

A compound of formula (I) suitable as a catalyst or for the preparation of a catalyst system:

$$L^1\text{-X-}L^2 \qquad (I)$$

is provided, in which

X is a lower alkylene group, an arylene group or an alkarylene group;

$L^1$ is

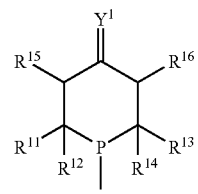

in which $Y^1$ is oxygen, sulfur or N—$R^{17}$, $R^{11}$, $R^{12}$, $R^{13}$, $R^{14}$, $R^{15}$, $R^{16}$ and $R^{17}$ independently of one another being hydrogen, alkyl or aryl; and $L^2$ is

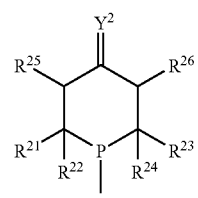

in which $Y^2$ is oxygen, sulfur or N—$R^{27}$, $R^{21}$, $R^{22}$, $R^{23}$, $R^{24}$, $R^{25}$, $R^{26}$ and $R^{27}$ independently of one another being hydrogen, alkyl or aryl, it being possible for $L^1$ and $L^2$ to be identical or different.

18 Claims, No Drawings

COMPOUND SUITABLE FOR USE AS A CATALYST OR FOR PRODUCING A CATALYST SYSTEM DERIVED FROM A BIS-PHOSPHORINANE

The present invention relates to a compound of formula (I) suitable as a catalyst or for the preparation of a catalyst system:

$$L^1\text{-}X\text{-}L^2 \qquad (I)$$

in which

X is a lower alkylene group, an arylene group or an alkarylene group;

$L^1$ is

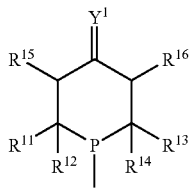

in which $Y^1$ is oxygen, sulfur or $N\!-\!R^{17}$, $R^{11}$, $R^{12}$, $R^{13}$, $R^{14}$, $R^{15}$, $R^{16}$ and $R^{17}$ independently of one another being hydrogen, alkyl or aryl; and $L^2$ is

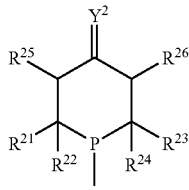

in which $Y^2$ is oxygen, sulfur or $N\!-\!R^{27}$, $R^{21}$, $R^{22}$, $R^{23}$, $R^{24}$, $R^{25}$, $R^{26}$ and $R^{27}$ independently of one another being hydrogen, alkyl or aryl, it being possible for $L^1$ and $L^2$ to be identical or different.

It further relates to a process for the preparation of a compound of formula (I), to the use of a compound of formula (I), to systems (VI) suitable as catalysts and obtainable by reaction with a compound of formula (I), and to processes for the carbonylation of olefinically unsaturated compounds in the presence of a compound of formula (I) or a system of formula (VI).

Processes for the catalytic carbonylation of olefinically unsaturated compounds, i.e. for their reaction with carbon monoxide and a compound containing a hydroxyl group, in the presence of a catalyst, to give an acid or derivatives thereof, are generally known.

Thus, for example, the carbonylation of n-pentenoic acid or derivatives thereof of formula (XII) can give adipic acid or derivatives thereof, which are extensively used in the manufacture of industrially important polymers, especially polyamides.

Processes for the carbonylation of n-pentenoic acid or derivatives thereof of formula (I) are disclosed for example in GB-1497046, DE-A-2541640, U.S. Pat. No. 4,508,660, EP-A-373579, U.S. Pat. No. 4,933,483, EP-A-450577, U.S. Pat. No. 4,257,973, WO 2000/14055, EP-A-577204, WO 2000/56695, EP-A-662467 or WO 2000/42717.

The carbonylation of olefinically unsaturated compounds (except for ethylene) normally gives linear and branched products.

In the case of the carbonylation of n-pentenoic acid, only the linear products are used extensively, while the branched products are of no importance or are only of secondary importance as far as quantity is concerned.

What is desirable, therefore, is a high n/i ratio coupled with a high yield. The n/i ratio is understood as meaning the ratio of the selectivity in respect of linear products to the selectivity in respect of branched products. The term linearity used in this connection in the state of the art denotes the selectivity in respect of linear products. The n/i ratio is calculated from the linearity according to the equation $$n/i \text{ ratio} = \text{linearity } [\%]/(100\% - \text{linearity } [\%])$$

The n/i ratio coupled with a high yield is unsatisfactory in said processes.

Thus, in Example 6 of U.S. Pat. No. 4,933,483, an n/i ratio of 24 (linearity 96%) is achieved for a yield of only 70%.

WO 98/42717, Example 7, discloses a yield of 84% (conversion 100%, selectivity 84%); however, the n/i ratio is only 5.25 (84% of linear product, the remainder being 16% of branched product).

It is an object of the present invention to provide a compound suitable as a catalyst or for the preparation of a system suitable as a catalyst, which compound avoids said disadvantages in a technically simple and economic manner.

We have found that this object is achieved by the compound of formula (I) defined at the outset, by a process for the preparation of a compound of formula (I), by the use of a compound of formula (I), by systems (VI) suitable as catalysts and obtainable by reaction with a compound of formula (I), and by processes for the carbonylation of olefinically unsaturated compounds in the presence of a compound of formula (I) or a system of formula (VI).

According to the invention, the compound of formula (I) has the structure $$L^1\text{-}X\text{-}L^2 \qquad (I).$$

Possible meanings of X are a lower alkylene group preferably having from 1 to 6 and especially from 1 to 4 carbon atoms between the two radicals $L^1$ and $L^2$, particularly preferably methylene, 1,2-ethylene, 1,3-propylene or 1,4-butylene, an arylene group, preferably 1,2-phenylene, 1,3-phenylene or 1,4-phenylene, or an alkarylene group, preferably 1,2-benzylidene, 1,3-benzylidene, 1,4-benzylidene, 1,2-xylylidene, 1,3-xylylidene or 1,4-xylylidene.

In one preferred embodiment, it is possible to use a lower alkylene group preferably having from 1 to 6 and especially from 1 to 4 carbon atoms between the two radicals $L^1$ and $L^2$, particularly preferably methylene, 1,2-ethylene, 1,3-propylene or 1,4-butylene.

The arylene group, alkylene group or alkarylene group can carry substituents such as alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy, but it preferably carries no substituents.

One or more carbon atoms in the arylene group, alkylene group or alkarylene group can be replaced with heteroatoms such as nitrogen, oxygen, sulfur or silicon, it being possible for the heteroatom(s), independently of one another and independently of the remaining structure of X, and according to the particular valency, to carry substituents such as hydrogen, alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy. Preferably, carbon in the arylene group, alkylene group or alkarylene group is not replaced with heteroatoms.

A possible meaning of $L^1$ is a structure of the formula

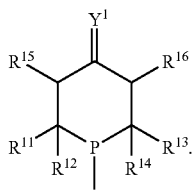

In this formula, $Y^1$ is oxygen, sulfur or $N-R^{17}$, preferably oxygen. Possible groups $R^{11}$, $R^{12}$, $R^{13}$, $R^{14}$, $R^{15}$, $R^{16}$ and $R^{17}$ independently of one another are hydrogen, alkyl, preferably alkyl having from one to 6 and especially from one to 4 carbon atoms, or aryl such as phenyl or p-tolyl.

In one preferred embodiment, the groups $R^{11}$, $R^{12}$, $R^{13}$, $R^{14}$, $R^{15}$, $R^{16}$ and $R^{17}$ used can independently of one another be a radical selected from the group comprising hydrogen, methyl, ethyl, n-propyl, i-propyl, n-butyl, i-butyl, s-butyl and t-butyl.

The groups $R^{11}$, $R^{12}$, $R^{13}$, $R^{14}$, $R^{15}$, $R^{16}$ and $R^{17}$ can independently of one another carry substituents such as alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy, but they preferably carry no substituents.

In the groups $R^{11}$, $R^{12}$, $R^{13}$, $R^{14}$, $R^{15}$, $R^{16}$ and $R^{17}$, one or more carbon atoms can independently of one another be replaced with heteroatoms such as nitrogen, oxygen, sulfur or silicon, it being possible for the heteroatom(s), independently of one another and independently of the remaining structure of X, and according to the particular valency, to carry substituents such as hydrogen, alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy. Preferably, carbon in the groups $R^{11}$, $R^{12}$, $R^{13}$, $R^{14}$, $R^{15}$, $R^{16}$ and $R^{17}$ is not replaced with heteroatoms.

A possible meaning of $L^2$ is a structure of the formula

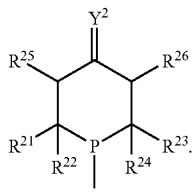

In this formula, $Y^2$ is oxygen, sulfur or $N-R^{27}$, preferably oxygen.

Possible groups $R^{21}$, $R^{22}$, $R^{23}$, $R^{24}$, $R^{25}$, $R^{26}$ and $R^{27}$ independently of one another are hydrogen, alkyl, preferably alkyl having from one to 6 and especially from one to 4 carbon atoms, or aryl such as phenyl or p-tolyl.

In one preferred embodiment, the groups $R^{21}$, $R^{22}$, $R^{23}$, $R^{24}$, $R^{25}$, $R^{26}$ and $R^{27}$ used can independently of one another be a radical selected from the group comprising hydrogen, methyl, ethyl, n-propyl, i-propyl, n-butyl, i-butyl, s-butyl and t-butyl.

The groups $R^{21}$, $R^{22}$, $R^{23}$, $R^{24}$, $R^{25}$, $R^{26}$ and $R^{27}$ can independently of one another carry substituents such as alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy, but they preferably carry no substituents.

In the groups $R^{21}$, $R^{22}$, $R^{23}$, $R^{24}$, $R^{25}$, $R^{26}$ and $R^{27}$, one or more carbon atoms can independently of one another be replaced with heteroatoms such as nitrogen, oxygen, sulfur or silicon, it being possible for the heteroatom(s), independently of one another and independently of the remaining structure of X, and according to the particular valency, to carry substituents such as hydrogen, alkyl groups, for example methyl, ethyl, n-propyl, i-propyl, n-butyl, i-butyl, s-butyl or t-butyl, aryl groups, for example phenyl or p-tolyl, halogens, for example fluorine, chlorine or bromine, alkoxy and aryloxy. Preferably, carbon in the groups $R^{21}$, $R^{22}$, $R^{23}$, $R^{24}$, $R^{25}$, $R^{26}$ and $R^{27}$ is not replaced with heteroatoms.

The radicals $L^1$ and $L^2$ can be identical or different, but are preferably identical.

A compound of formula (I) can advantageously be prepared by reacting a compound of formula (II):

$$H_2P-X-PH_2 \qquad (II)$$

with a compound of formula (IV):

$$(R^{11}R^{12}C)=(CR^{13})-(C=Y^1)-(CR^{14})=(CR^{15}R^{16}) \qquad (IV)$$

and a compound of formula (V):

$$(R^{21}R^{22}C)=(CR^{23})-(C=Y^2)-(CR^{24})=(CR^{25}R^{26}) \qquad (V)$$

$R^{11}$, $R^{12}$, $R^{13}$, $R^{14}$, $R^{15}$, $R^{16}$, $R^{21}$, $R^{22}$, $R^{23}$, $R^{24}$, $R^{25}$, $R^{26}$, $Y^1$, $Y^2$ and X being as defined above.

Advantageous process conditions which can be used for the preparation are the process conditions for the preparation of 4-phosphorinanones according to Richard P. Welcher and Nancy E. Day, J. Am. Chem. Soc., 27 (1962) 1824–1827.

Compounds of formula (I), either as individual substances or as a mixture, can be used as catalysts or as constituents of systems suitable as catalysts.

Thus a catalyst containing a compound of formula (I) can be used in a process for the carbonylation of olefinically unsaturated compounds (X) by reacting a compound of formula (X) with carbon monoxide and a compound (IX) containing a hydroxyl group.

A system (VI) suitable as a catalyst can advantageously be obtainable by reacting
  a) a source of an ion of a metal (VII) of subgroup VIII of the Periodic Table of the Elements with
  b) a compound of formula (I) as described above.

Possible metals (VII) are those of subgroup VIII of the Periodic Table, such as iron, cobalt, nickel, ruthenium, rhodium, palladium, osmium, iridium and platinum, preferably palladium, platinum, rhodium and iridium and especially palladium, and mixtures thereof.

Sources of an ion of such a metal which can advantageously be used are salts of such metals, or compounds in which such a metal has a weak coordinate bond, with anions derived from mineral acids such as nitric acid, sulfuric acid or phosphoric acid, carboxylic acids, advantageously $C_1$–$C_{12}$ carboxylic acids and preferably acetic acid, propionic acid or butyric acid, sulfonic acids such as methanesulfonic acid, chlorosulfonic acid, fluorosulfonic acid, trifluoromethanesulfonic acid, benzenesulfonic acid, naphthalenesulfonic acid, toluenesulfonic acid, especially p-toluenesulfonic acid, t-butylsulfonic acid or 2-hydroxypropanesulfonic acid, sulfonated ion exchangers, halogenated per acids such as perchloric acid, perfluorinated carboxylic acids such as trifluoroacetic acid, nonafluorobutanesulfonic acid or trichloroacetic acid, phosphonic acids such as benzenephosphonic acid, or acids derived from the interaction of Lewis acids with Broensted acids, anions such as tetraphenylborate and derivatives thereof, or mixtures of said anions.

It is also possible advantageously to use compounds in which such a metal is in the zerovalent form with readily cleavable ligands, for example tris(dibenzylideneacetone) palladium, tetrakis(triphenylphosphine)palladium and bis (tri-o-tolylphosphine)palladium.

Possible compounds of formula (I) are advantageously those which exhibit a chelating action when reacting with a metal (VII) or metal ion (VII).

The molar ratio of compound (I) to metal (VII) can be chosen within wide limits. A possible ratio advantageously ranges from 0.5 to 50, preferably from 0.5 to 20, particularly preferably from 0.5 to 10 and especially from 1 to 5 mol/mol.

In one preferred embodiment, the catalyst system is obtainable in the presence of an anion source (IX).

Anion sources which can be used are compounds already containing the anion, such as salts, or compounds capable of releasing an anion by a chemical reaction such as heterolytic bond scission.

Suitable anion sources are disclosed for example in EP-A-495 547.

Anion sources (IX) which can advantageously be used are compounds capable of generating an anion by elimination of an H$^+$ ion, such as nitric acid, sulfuric acid, phosphoric acid, carboxylic acids, advantageously $C_1$–$C_{20}$ carboxylic acids and preferably acetic acid, propionic acid, 2,4,6-trimethylbenzoic acid, 2,6-dichlorobenzoic acid, 9-anthracenecarboxylic acid, pivalic acid, 1,2,3-benzenetricarboxylic acid, 1,2,3-benzenetricarboxylic acid 1,3 diesters, 2-ethoxy-1-naphthalenecarboxylic acid, 2,6-dimethoxybenzoic acid or 5-cyanovaleric acid, sulfonic acids such as methanesulfonic acid, chlorosulfonic acid, fluorosulfonic acid, trifluoromethanesulfonic acid, benzenesulfonic acid, naphthalenesulfonic acid, toluenesulfonic acid, especially p-toluenesulfonic acid, t-butylsulfonic acid or 2-hydroxypropanesulfonic acid, sulfonated ion exchangers, halogenated per acids such as perchloric acid, perfluorinated carboxylic acids such as trifluoroacetic acid, nonafluorobutanesulfonic acid or trichloroacetic acid, phosphonic acids such as benzenephosphonic acid, acids derived from the reaction of a Lewis acid such as $BF_3$, $PF_5$, $AsF_5$, $SbF_5$, $TaF_5$ or $NbF_5$ with a Broensted acid such as HF (for example fluosilicic acid, $HBF_4$, $HPF_6$, $HSbF_6$, tetraphenylboric acid and derivatives thereof), or mixtures of said compounds.

Preferred compounds (IX) capable of generating an anion by elimination of an H$^+$ ion are those with a $PK_a$ of at most 3.5 and especially of at most 2.

The molar ratio of compound (IX) to metal (VII) is not critical per se. The molar ratio of compound (IX) to metal (VII) can advantageously range from 0.5 to 100 and preferably from 1 to 20 mol/mol.

According to the invention, in a process for the carbonylation of olefinically unsaturated compounds (X) by reacting a compound of formula (X) with carbon monoxide and a compound (XI) containing a hydroxyl group, in the presence of a catalyst system, it is possible to use a catalyst which contains a system (VI) or, preferably, consists of such a system.

In principle, internally and terminally olefinically unsaturated compounds can be used, without limitation, as compounds (X). The compound (X) can have one or more, such as two or three, units of olefinic unsaturation, preferably one unit of olefinic unsaturation.

In one preferred embodiment, the olefinically unsaturated compound can advantageously be a substituted or unsubstituted alkene or cycloalkene having preferably from 2 to 30, especially from 2 to 20 and particularly preferably from 2 to 10 carbon atoms in the molecule. The alkene or cycloalkene can be substituted for example by one or more halogen atoms or cyano, ester, carboxyl, amino, amido, nitrile, alkoxy, aryl or thioalkoxy groups. Examples of olefinically unsaturated compounds (X) are ethene, propene, 1-butene, 2-butene, isobutene, the isomeric pentenes, hexenes, octenes such as 1-octene, 2,4,4-trimethyl-1-pentene and 2,4,4-trimethyl-2-pentene, and dodecenes, 1,5-cyclooctadiene, cyclododecene, acrylic acid, methyl acrylate, ethyl acrylate, acrylonitrile, acrylamide, an N,N-dialkylacrylamide, acrylaldehyde, methyl methacrylate, the isomeric pentenoic acids, the isomeric methyl pentenoates, the isomeric pentene nitriles, vinyl chloride, ethyl vinyl ketone, allyl chloride, methyl allyl ether and styrene.

In another preferred embodiment, a possible compound (X) is an optionally substituted, olefinically unsaturated compound with at least one terminal olefinic bond, especially an optionally substituted alpha-olefin. Preferred optionally substituted, olefinically unsaturated compounds can be represented by formula (XIII):

$$H_2C=(C\ Y^3\ Y^4)  \qquad (XIII)$$

in which $Y^3$ is hydrogen or a hydrocarbyl group and $Y^4$ is hydrogen or an electron-withdrawing or electron-donating substituent such as carboxyl, nitrile, formyl, amino or halogen, or a substituent of the formula $Y^5$—$R^{41}$, in which $Y^5$ is a single bond or the functional group —CO—, —COO—, —OOC—, —NH—, —CONH—, —NHCO—, —O— or —S—, and $R^{41}$ is an optionally substituted alkyl, alkenyl, cycloalkyl, cycloalkenyl, aryl or heterocyclic group. A possible alkyl group is advantageously a $C_1$- to $C_{10}$-alkyl group, especially a $C_1$- to $C_6$-alkyl group such as methyl, ethyl, n-propyl, i-propyl, n-butyl, i-butyl, s-butyl, t-butyl or n-hexyl. A cycloalkyl group which can advantageously be used is a $C_3$- to $C_6$-cycloalkyl group such as cyclopentyl or cyclohexyl. The alkenyl and cycloalkenyl groups can advantageously have the same number of carbon atoms and a carbon-carbon double bond in any position. The aryl group can advantageously be a phenyl or naphthyl group. The heterocyclic group should preferably have from 3 to 12 atoms, including 1, 2 or 3 heteroatoms such as oxygen, sulfur or nitrogen.

In another preferred embodiment, the compounds (X) used can be nucleophiles with a mobile hydrogen, including alkenoic acid derivatives such as alkenoic acids, alkenoic anhydrides, alkenoic acid amides, alkenoic acid nitriles or alkenoic acid esters. The acid group can be located directly adjacent to the olefinic double bond, for example it can be a 2-alkenoic acid derivative. The alkenyl group of the alkenoic acid can be substituted or, preferably, unsubstituted, such as vinyl, 1-propenyl, 1-butenyl, 1-pentenyl or 1-hexenyl, and can advantageously have from 2 to 12 carbon atoms. Possible examples are acrylic acid, methacrylic acid, 2-butenoic acid, 2-pentenoic acid, acrylonitrile, methacrylonitrile, 2-butene nitrile, 2-pentene nitrile, acrylamide, methacrylamide, 2-butenamide, 2-pentenamide, an N-substituted acrylamide, an N-substituted methacrylamide, an N-substituted 2-butenamide, an N-substituted 2-pentenamide or an ester of said alkenoic acids. The N-substituents of the amide group and the O-substituents of the ester group can be aliphatic, cycloaliphatic or aromatic and unsubstituted or substituted, and can preferably have from 1 to 10 carbon atoms. Examples of these are methyl acrylate, ethyl acrylate, phenyl acrylate, n-propyl acrylate, i-propyl acrylate, n-butyl acrylate, i-butyl acrylate, t-butyl acrylate, s-butyl acrylate, the corresponding methacrylates, 2-butenates, 2-pentenates, N,N-dimethylacrylamide and the corresponding methacrylamides, 2-butenamides and 2-pentenamides.

In another preferred embodiment, as the compound (X), it is possible to carbonylate an unsubstituted alpha-olefin in the presence of a nucleophile with a mobile hydrogen to give an ester or other carbonyl compound.

In another preferred embodiment, a compound (X) which can be used is n-pentenoic acid or derivatives thereof of formula (XII):

this also being understood in terms of the present invention as meaning mixtures of such compounds.

A possible radical $R^{31}$ is —CN or $COOR^{32}$, it being possible for $R^{32}$ to be hydrogen, alkyl or aryl, advantageously hydrogen or alkyl, preferably hydrogen, methyl, ethyl, n-propyl, i-propyl, n-butyl, i-butyl, s-butyl or t-butyl, especially hydrogen, methyl or ethyl and particularly preferably hydrogen or methyl.

If $R^{32}$ is an alkyl or aryl group, it can carry substituents such as functional groups or other alkyl or aryl groups. An alkyl or aryl group $R^2$ preferably carries no substituents.

In principle, a possible n-pentenoic acid or derivative thereof of formula (XII) is any of the isomers, such as the cis-2, trans-2, cis-3, trans-3 or 4 isomer, or mixtures thereof. Such mixtures can contain the same radical $R^{31}$ or different radicals $R^{31}$. Preferred mixtures are those containing the same radical $R^{31}$.

It is advantageous to use cis-2-, trans-2-, cis-3-, trans-3- or 4-pentene nitrile or mixtures thereof. Preferred mixtures are those containing at least 80% by weight of 3-pentene nitrile, i.e. cis-3-pentene nitrile and trans-3-pentene nitrile together.

In another advantageous embodiment, it is possible to use cis-2-, trans-2-, cis-3-, trans-3- or 4-pentenoic acid or mixtures thereof. Preferred mixtures are those containing at least 80% by weight of 3-pentenoic acid, i.e. cis-3-pentenoic acid and trans-3-pentenoic acid together.

In another advantageous embodiment, it is possible to use methyl cis-2-, trans-2-, cis-3-, trans-3- or 4-pentenoate or mixtures thereof. Preferred mixtures are those containing at least 80% by weight of methyl 3-pentenoate, i.e. methyl cis-3-pentenoate and methyl trans-3-pentenoate together.

Pentenoic acid and derivatives thereof of formula (XII) can be obtained by processes known per se, for example by the addition of carbon monoxide and a compound containing a hydroxyl group, or the addition of hydrogen cyanide, onto butadiene in the presence of a catalyst.

The molar ratio of metal (VII) to compound (X) is not critical per se. A molar ratio of metal (VII) to compound (X) ranging from $10^{-7}:1$ to $10^{-1}:1$, preferably from $10^{-6}:1$ to $10^{-2}:1$ has proved advantageous.

According to the invention, the compound of formula (X) is reacted with carbon monoxide. The carbon monoxide can be used as the pure compound or in the presence of gases which substantially do not adversely affect the process according to the invention, especially gases with an inert behavior. Examples of possible inert gases are nitrogen, hydrogen, carbon dioxide, methane and the noble gases such as argon.

Advantageously, the molar ratio of compound (X) to carbon monoxide can be at least 1:1, preferably at least 3:1, especially at least 5:1, preferably in the range from 5:1 to 50:1 and particularly preferably in the range from 7:1 to 15:1. If the process according to the invention is carried out with molar ratios of compound (I) to carbon monoxide of less than 5:1, especially of less than 3:1 and particularly of less than 1:1, this can result in a rapid impairment of the properties of the catalyst system.

According to the invention, the compound of formula (X) is reacted with a compound (XI) containing a hydroxyl group. Compounds (XI) are understood in terms of the present invention as meaning individual compounds (XI) as well as mixtures of different compounds of this type.

The type of compound (XI) at least partially determines the end product of the present process. If water is used as the compound (XI), the corresponding acid is obtained, whereas if an alcohol such as an alkanol is used, the corresponding ester is obtained. Possible alcohols are primary, secondary or tertiary alcohols, preferably primary alcohols, and advantageously $C_1$–$C_{30}$ alkanols which can optionally carry substituents such as one or more halogen, nitrile, carbonyl, alkoxy or aryl groups. Possible alkanols are advantageously methanol, ethanol, n-propanol, i-propanol, n-butanol, i-butanol, s-butanol, t-butanol, n-hexanol, n-octanol, i-octanol, 2-ethylhexanol, cyclohexanol, benzyl alcohol, phenylethyl alcohol, ethylene glycol, 1,2-propanediol, 1,3-propanediol, neopentyl glycol, trimethylolpropane or pentaerythritol, preferably methanol, ethanol, n-propanol, i-propanol, n-butanol, i-butanol, s-butanol or t-butanol, particularly preferably methanol or ethanol and especially methanol.

The molar ratio of compound (X) to compound (XI) is not critical per se and can vary within wide limits, advantageously ranging from 0.001:1 to 100:1 mol/mol.

The catalyst system can be prepared before being used in the process according to the invention or during the actual process according to the invention.

If the catalyst system is prepared during the actual process according to the invention, it has proved advantageous to use metal compounds (III) which are soluble in the reaction mixture to the extent that they can form an active catalyst system with the other components.

The catalyst system employed in the process according to the invention can be used in the heterogeneous or, preferably, homogeneous phase.

The catalyst system can advantageously be obtained in the liquid phase. The liquid phase can be formed of one or more of the components from which the catalyst system is obtainable or has been obtained. Another possibility is to prepare the liquid phase using an inorganic or, preferably, organic liquid diluent.

Possible liquid diluents are advantageously aprotic liquid diluents such as ethers, for example diethyl ether, dimethyl ether, ethylene glycol dimethyl ether, diethylene glycol dimethyl ether, tetrahydrofuran, polyethers, functionalized polyethers, anisole, 2,5,8-trioxanonane, diisopropyl ether and diphenyl ether, aromatics, including halogenated aromatics, for example benzene, toluene, o-xylene, m-xylene, p-xylene, chlorobenzene, o-dichlorobenzene, m-dichlorobenzene and p-dichlorobenzene, alkanes, including halogenated alkanes, for example hexane, heptane, 2,2,3-trimethylpentane, methylene dichloride and carbon tetrachloride, nitriles, for example benzonitrile and acetonitrile, esters, for example methyl benzoate, methyl acetate, dimethyl phthalate and butyrolactone, sulfones, for example diethyl sulfone, diisopropyl sulfone, tetrahydrothiophene 1,1-dioxide ("sulfolan"), 2-methylsulfolan, 3-methylsulfolan and 2-methyl-4-butylsulfolan, sulfoxides, for example dimethyl sulfoxide, amides, including halogenated amides, for example dimethylformamide, dimethylacetamide and N-methylpyrrolidone, ketones, for example acetone, methyl ethyl ketone and methyl isobutyl ketone, and mixtures thereof.

Particularly preferred liquid diluents are those whose boiling point is higher than that of the particular product obtained by the process according to the invention. This can facilitate the separation of the product from the remaining reaction mixture, for example by distillation.

The process according to the invention can advantageously be carried out at a temperature ranging from 20 to 250° C., preferably from 40 to 200° C., particularly preferably from 70 to 170° C. and especially from 80 to 140° C.

The process according to the invention can advantageously be carried out under a total pressure of $1*10^5$ to $200*10^5$ Pa, preferably of $5*10^5$ to $70*10^5$ Pa and especially of $6*10^5$ to $20*10^5$ Pa.

The process according to the invention can be carried out continuously, batchwise or semicontinuously.

The product of the process can be separated from the other components by methods known per se, such as extraction or distillation.

By virtue of the high n/i ratio in the process according to the invention, the subsequent purification cost can be markedly reduced as fewer unwanted by-products are obtained.

Another advantage of the process according to the invention is that the remaining components containing the catalyst system can be recycled into the process according to the invention, it being possible for fresh catalyst to be added if desired.

EXAMPLES

Preparation of Compounds of Formula (I)

Example 1

14.6 g (0.106 mol) of 2,6-dimethyl-2,5-heptadien-4-one ("phorone") and 5.0 g (0.053 mol) of 1,2-bisphosphinoethane were brought together in a Schlenk tube and stirred for 20 hours at 120° C. The light yellow solid formed was washed with 2×20 ml of pentane and then dried under reduced pressure to give a white powder. The product was characterized by means of $^{31}$P NMR spectroscopy, elemental analysis and GC/MS.

Yield: 18.2 g, corresponding to 93% of theory

Example 2

The procedure of Example 1 was followed except that the 1,2-bisphosphinoethane was replaced with 5.7 g (0.053 mol) of 1,3-bisphosphinopropane.

Yield: 18.7 g, corresponding to 92% of theory

Example 3

The procedure of Example 1 was followed except that the 1,2-bisphosphinoethane was replaced with 6.5 g (0.053 mol) of 1,3-bisphosphinopropane Yield: 19.9 g, corresponding to 94% of theory.

Example 4

The procedure of Example 1 was followed except that the 1,2-bisphosphinoethane was replaced with 7.5 g (0.053 mol) of 1,2-bisphosphinobenzene.

Yield: 19.9 g, corresponding to 86% of theory

Example 5

The procedure of Example 1 was followed except that 2 g (0.021 mol) of 1,2-bisphosphinoethane and 10 g (0.0427 mol) of dibenzylideneacetone were used.

Yield: 11.0 g, corresponding to 92% of theory

Example 6

The procedure of Example 5 was followed except that the 1,2-bisphosphinoethane was replaced with 2.3 g (0.021 mol) of 1,3-bisphosphinopropane.

Yield: 11.1 g, corresponding to 90% of theory

Preparation of Systems of Formula (VI)

Example 7

8.5 g (0.023 mol) of 1,2-bis(4-phosphorinone)ethane of Example 1 were dissolved in 50 ml of acetone and the solution was slowly added dropwise to a solution of palladium diacetate in 50 ml of acetone. The yellow solid which immediately precipitated out was separated off by means of a frit, washed with 2×20 ml of toluene and dried under reduced pressure.

Yield: 13.2 g, corresponding to 96% of theory

Example 8

The procedure of Example 7 was followed except that the 1,2-bis(4-phosphorinone)ethane was replaced with 8.8 g (0.023 mol) of 1,2-bis(4-phosphorinone)propane of Example 2.

Yield: 13.5 g, corresponding to 96% of theory

Example 9

The procedure of Example 7 was followed except that the 1,2-bis(4-phosphorinone)ethane was replaced with 9.2 g (0.023 mol) of 1,2-bis(4-phosphorinone)butane of Example 3.

Yield: 13.8 g, corresponding to 96% of theory

Carbonylation of Ethene

Example 10

28 mg (0.12 mmol) of palladium diacetate, 81 mg (0.22 mmol) of 1,2-bis(4-phosphorinone)ethane of Example 1, 94 mg (0.5 mmol) of p-toluenesulfonic acid and 150 ml of n-butanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa) for a molar ratio of carbon monoxide to ethene of 1:1. After one hour the autoclave was cooled, the pressure was released and the liquid discharge was examined by gas chromatography. No deposition of palladium was observed.

The results are collated in Table 1.

Example 11

28 mg (0.12 mmol) of palladium diacetate, 81 mg (0.22 mmol) of 1,2-bis(4-phosphorinone)ethane of Example 1, 60 mg (0.6 mmol) of methanesulfonic acid and 150 ml of n-butanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa) for a molar ratio of carbon monoxide to ethene of 1:1. After one hour the autoclave was cooled, the pressure was released and the liquid discharge was examined by gas chromatography. No deposition of palladium was observed.

The results are collated in Table 1.

Example 12

28 mg (0.12 mmol) of palladium diacetate, 81 mg (0.22 mmol) of 1,2-bis(4-phosphorinone)ethane of Example 1, 410 mg (23 mmol) of water and 150 ml of n-butanol were placed in a 400 ml glass autoclave with a gas dispersion stirrer. After sealing, a carbon monoxide pressure of 4 bar ($4*10^5$ Pa) was applied. The autoclave was heated to 140° C. and the total pressure was adjusted to 7 bar ($7*10^5$ Pa) for a molar ratio of carbon monoxide to ethene of 1:1. After one hour the autoclave was cooled, the pressure was released and the liquid discharge was examined by gas chromatography. No deposition of palladium was observed.

The results are collated in Table 1.

Example 13

28 mg (0.12 mmol) of palladium diacetate, 81 mg (0.22 mmol) of 1,2-bis(4-phosphorinone)ethane of Example 1, 245 mg (0.1 mmol) of 9-anthracenecarboxylic acid and 150 ml of n-butanol were placed in a 400 ml glass autoclave with a gas dispersion stirrer. After sealing, a carbon monoxide pressure of 4 bar ($4*10^5$ Pa) was applied. The autoclave was heated to 140° C. and the total pressure was adjusted to 7 bar ($7*10^5$ Pa) for a molar ratio of carbon monoxide to ethene of 1:1. After one hour the autoclave was cooled, the pressure was released and the liquid discharge was examined by gas chromatography. No deposition of palladium was observed.

The results are collated in Table 1.

Example 14

36 mg (0.06 mmol) of the system of Example 7, 30 mg (0.3 mmol) of methanesulfonic acid and 150 ml of n-butanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa) for a molar ratio of carbon monoxide to ethene of 1:1. After one hour the autoclave was cooled, the pressure was released and the liquid discharge was examined by gas chromatography. No deposition of palladium was observed.

The results are collated in Table 1.

TABLE 1

| Example | Conversion of n-butanol [%] | TOF [$h^{-1}$] | Selectivity in respect of propionic acid ester [%] |
|---|---|---|---|
| 10 | 80 | 10950 | >99 |
| 11 | 95 | 12900 | >99 |
| 12 | 50 | 6840 | >99 |
| 13 | 45 | 6150 | >99 |
| 14 | 98 | 26700 | >99 |

TOF: Turnover frequency (mol product/mol catalyst/hour)
Carbonylation of 3-pentene nitrile

Example 15

70 mg (0.31 mmol) of palladium diacetate, 230 mg (0.62 mmol) of 1,2-bis(4-phosphorinone)ethane of Example 1, 590 mg (3.1 mmol) of p-toluenesulfonic acid, 80 ml (830 mmol) of 3-pentene nitrile and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 2.

Example 16

70 mg (0.31 mmol) of palladium diacetate, 240 mg (0.62 mmol) of 1,3-bis(4-phosphorinone)propane of Example 2, 590 mg (3.1 mmol) of p-toluenesulfonic acid, 80 ml (830 mmol) of 3-pentene nitrile and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 2.

Example 17

123 mg (0.2 mmol) of system (VI) of Example 8, 380 mg (2.0 mmol) of p-toluenesulfonic acid, 80 ml (830 mmol) of 3-pentene nitrile and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 2.

TABLE 2

| Ex. | Conversion of 3-PN [%] | TOF [$h^{-1}$] | Carbonylation selectivity [%] | Selectivity in respect of n [%] |
|---|---|---|---|---|
| 15 | 70 | 1705 | 91 | 80.5 |
| 16 | 94 | 2500 | >99 | 97.2 |
| 17 | 95 | 3900 | >99 | 98.3 |

3-PN: 3-pentene nitrile
TOF: Turnover frequency (mol product/mol catalyst/hour)
Carbonylation of methyl 3-pentenoate

Example 18

70 mg (0.31 mmol) of palladium diacetate, 230 mg (0.62 mmol) of 1,2-bis(4-phosphorinone)ethane of Example 1, 590 mg (3.1 mmol) of p-toluenesulfonic acid, 102 ml (840 mmol) of methyl 3-pentenoate and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 3.

Example 19

70 mg (0.31 mmol) of palladium diacetate, 240 mg (0.62 mmol) of 1,3-bis(4-phosphorinone)propane of Example 2, 590 mg (3.1 mmol) of p-toluenesulfonic acid, 102 ml (840 mmol) of methyl 3-pentenoate and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 3.

Example 20

123 mg (0.2 mmol) of system (VI) of Example 8, 380 mg (2.0 mmol) of p-toluenesulfonic acid, 102 ml (840 mmol) of methyl 3-pentenoate and 34 ml of methanol were placed in a 400 ml glass autoclave with a gas dispersion stirrer. After sealing, a carbon monoxide pressure of 4 bar ($4*10^5$ Pa) was applied. The autoclave was heated to 90° C. and the total pressure was adjusted to 7 bar ($7*10^5$ Pa). After one hour the autoclave was cooled, the pressure was released and the liquid discharge was examined by gas chromatography. No deposition of palladium was observed.

The results are collated in Table 3.

TABLE 3

| Ex. | Conversion of M 3-P [%] | TOF [h$^{-1}$] | Carbonylation selectivity [%] | Selectivity in respect of n [%] |
|---|---|---|---|---|
| 18 | 71 | 1770 | 92 | 80.6 |
| 19 | 95 | 2550 | >99 | 97.5 |
| 20 | 96 | 3990 | >99 | 98.4 |

M 3-P: methyl 3-pentenoate
TOF: Turnover frequency (mol product/mol catalyst/hour)

We claim:

1. A compound of formula (I):

$$L^1-X-L^2 \quad (I)$$

in which

X is a lower alkylene group, an arylene group or an alkarylene group;

$L^1$ is

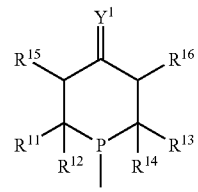

in which $Y^1$ is oxygen, sulfur or N—$R^{17}$, $R^{12}$, $R^{14}$, $R^{15}$, $R^{16}$ and $R^{17}$ independently of one another being hydrogen, alkyl or aryl; and $R^{11}$ and $R^{13}$ independently of one another being alkyl or ayrl, $L^2$ is

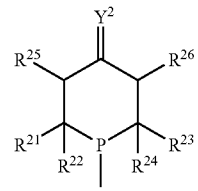

in which $Y^2$ is oxygen, sulfur or N—$R^{27}$, $R^{22}$, $R^{24}$, $R^{25}$, $R^{26}$ and $R^{27}$ independently of one another being hydrogen, alkyl or aryl, $R^{21}$ and $R^{23}$ independently of one another being alkyl or aryl, it being possible for $L^1$ and $L^2$ to be identical or different.

2. The compound of formula (I) as claimed in claim 1 in which $L^1$ and $L^2$ are identical.

3. The compound of formula (I) as claimed in claim 1 in which X is a lower alkylene group.

4. The compound of formula (I) as claimed in claim 1 in which X is selected from the group consisting of methylene, 1,2-ethylene, 1,3-propylene and 1,4butylene.

5. The compound of formula (I) as claimed in claim 1 in which $Y^1$ and $Y^2$ are oxygen.

6. The compound of formula (I) as claimed in claim 1 in which $R^{11}$, $R^{12}$, $R^{13}$, $R^{14}$, $R^{16}$, $R^{17}$, $R^{21}$, $R^{23}$, $R^{24}$, $R^{25}$, $R^{26}$ and $R^{27}$, within the definitions as claimed in claim 1, independently of one another are selected from the group consisting of hydrogen, methyl, ethyl, n-propyl, i-propyl, n-butyl, i-butyl, s-butyl and t-butyl.

7. A process for the preparation of a compound of formula (I) as claimed in claim 1, wherein a compound of formula (II):

$$H_2P-X-PH_2 \quad (II)$$

is reacted with a compound of formula (IV):

$$(R^{11}R^{12}C)=(CR^{13})-(C=Y^1)-(CR^{14})=(CR^{15}R^{16}) \quad (IV)$$

and a compound of formula (V):

$$(R^{21}R^{22}C)=(CR^{23})-(C=Y^2)=(CR^{24})=(CR^{25}R^{26}) \quad (V)$$

$R^{11}$, $R^{12}$, $R^{13}$, $R^{14}$, $R^{15}$, $R^{16}$, $R^{21}$, $R^{22}$, $R^{23}$, $R^{24}$, $R^{25}$, $R^{26}$, $Y^1$, $Y^2$ and X being as defined in claim 1.

8. A system suitable as a catalyst, obtained by reacting
a) a source of an ion of a metal of subgroup VIII of the Periodic Table of the Elements with
b) the compound of formula (I) as claimed in claim 1.

9. The system as claimed in claim 8 in which the metal is selected from the group consisting of palladium, platinum, rhodium and iridium.

10. The system as claimed in claim 8 in which the metal is palladium.

11. The system as claimed in claim 8 obtained in the presence of an anion source.

12. The system as claimed in claim 11 in which the anion source is a compound capable of generating an anion by elimination of an H$^+$ ion.

13. A process for the carbonylation of olefinically unsaturated compounds, said process comprising reacting a compound of formula (X) with carbon monoxide and a compound containing a hydroxyl group, in the presence of a catalyst, wherein the catalyst contains the compound of formula (I) as claimed in claim 1.

14. A process for the carbonylation of olefinically unsaturated compounds, said process comprising reacting an olefinically unsaturated compound with carbon monoxide and a compound containing a hydroxyl group, in the presence of a catalyst, wherein the catalyst contains the system as claimed in claim 8.

15. The process as claimed in claim 14 in which the olefinically unsaturated compound is n-pentenoic acid or a derivative thereof of formula (XII):

$$C_4H_7\text{—}R^{31} \qquad (XII)$$

in which $R^{31}$ is —CN or COOR$^{32}$, where $R^{32}$ is hydrogen, alkyl or aryl.

16. The process as claimed in claim 15 in which $R^{32}$ is selected from the group consisting of hydrogen, methyl, ethyl, n-propyl, i-propyl, n-butyl, i-butyl, s-butyl and t-butyl.

17. The process as claimed in claim 15 in which at least 80% by weight of the compound of formula (XII) is 3-pentene nitrile.

18. The process as claimed in claim 15 in which at least 80% by weight of the compound of formula (XII) is methyl 3-pentenoate.

* * * * *